(12) United States Patent
Young et al.

(10) Patent No.: US 10,751,016 B2
(45) Date of Patent: Aug. 25, 2020

(54) X-RAY IMAGE INHALATION QUALITY MONITORING

(71) Applicant: KONINKLIJKE PHILIPS N.V., Eindhoven (NL)

(72) Inventors: Stewart Young, Hamburg (DE); Jens Von Berg, Hamburg (DE); Daniel Bystrov, Hamburg (DE); Nataly Wieberneit, Hamburg (DE); Ulrich Neitzel, Hamburg (DE); Pallavi Vajinepalli, Bangalore (IN); Biswaroop Chakrabarti, Kolkata (IN); Soubhik Paul, Bangalore (IN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 151 days.

(21) Appl. No.: 15/774,414

(22) PCT Filed: Nov. 2, 2016

(86) PCT No.: PCT/EP2016/076312
§ 371 (c)(1),
(2) Date: May 8, 2018

(87) PCT Pub. No.: WO2017/080868
PCT Pub. Date: May 18, 2017

(65) Prior Publication Data
US 2018/0325481 A1    Nov. 15, 2018

(30) Foreign Application Priority Data
Nov. 9, 2015 (EP) .................................... 15193715

(51) Int. Cl.
*A61B 6/00* (2006.01)

(52) U.S. Cl.
CPC .............. *A61B 6/50* (2013.01); *A61B 6/5217* (2013.01); *A61B 6/541* (2013.01)

(58) Field of Classification Search
CPC ......... A61B 6/50; A61B 6/541; A61B 6/5217; G06T 7/0012
See application file for complete search history.

(56) References Cited

U.S. PATENT DOCUMENTS

| 5,485,833 A | 1/1996 | Dietz |
| 2001/0021264 A1* | 9/2001 | Armato, III .............. G06K 9/38 382/132 |

(Continued)

OTHER PUBLICATIONS

Koehler et al., "Knowledge-Assisted Reconstruction of the Human Rib Cage and Lungs", IEEE Computer Graphics and Applications, vol. 30, Issue 1, pp. 17-29 (Year: 2010).*

(Continued)

*Primary Examiner* — Nay A Maung
*Assistant Examiner* — Jose M Torres
(74) *Attorney, Agent, or Firm* — Larry Liberchuk (57) ABSTRACT

The quality of thoracic X-rays is depends on the inspiration state of an imaged patient. If the lungs of a patient are not significantly inflated during a thoracic X-ray, tissue from surrounding organs can cause the image to become cloudier, and the lung parenchyma is not effectively shown. Thus, there is a reliance on a medical professional to ensure that the patient is in an appropriate posture and inspiration state at the point of image exposure. This can be difficult with patients suffering from chronic conditions, though. Therefore, this application discusses a means to assess the inspiration state using the position of rib bones, and the diaphragm line in the X-ray image. Thus, an accurate estimate of inspiration state can automatically be reported to a medical professional, before a patient leaves the examination room, allowing an X-ray to be retaken, if necessary.

14 Claims, 5 Drawing Sheets

(56) References Cited

U.S. PATENT DOCUMENTS

| | | | |
|---|---|---|---|
| 2004/0161141 A1 | 8/2004 | Dewaele | |
| 2009/0087072 A1* | 4/2009 | Hong | G06T 7/12 |
| | | | 382/132 |
| 2010/0104070 A1 | 4/2010 | Knox | |
| 2010/0322493 A1* | 12/2010 | Wei | G06T 7/0014 |
| | | | 382/128 |
| 2013/0156267 A1 | 6/2013 | Muraoka | |
| 2014/0079309 A1 | 3/2014 | Huo | |
| 2014/0140603 A1 | 5/2014 | Huo | |
| 2015/0297164 A1 | 10/2015 | Dankerl | |
| 2019/0130561 A1* | 5/2019 | Katsuhara | G16H 30/40 |

OTHER PUBLICATIONS

Salito et al., "Alterations of diaphragm and rib cage morphometry in severe COPD patients by CT analsys", 2015 37th Annual International Conference of the IEEE Engineering in Medicine and Biology Society (EMBC), pp. 6390-6393 (Year: 2015).*

European Commission. European Guidelines on Quality Criteria for Diagnostic Radiographic Images. 1996.

Radiology Masterclass website → Tutorials → Chest → Quality (accessed Jan. 29, 2015) http://radiologymasterclass.co.uk/tutorials/chest/chest_quality/chest_xray_quality_inspiration.html ).

"Bone Suppression for Chest Radiographic Images", www.carestream.com, Mar. 2014.

* cited by examiner

X-RAY IMAGE INHALATION QUALITY MONITORING

FIELD OF THE INVENTION

The present invention relates to X-ray image inhalation quality monitoring, and in particular to an apparatus for X-ray image inhalation quality monitoring, a method for X-ray image inhalation quality monitoring, an X-ray imaging system, a computer program element, and a computer-readable medium.

BACKGROUND OF THE INVENTION

Chest X-ray screening is an important procedure for the detection and monitoring of lung abnormalities and diseases at an early stage in the lungs of patients. Medical personnel, such as doctors or radiologists, detect abnormalities directly from X-ray images. Assessing the image quality directly after acquisition is the task of a medical imaging professional. The image is checked as being of sufficient quality before the patient leaves the examination room. If the chest X-ray image is not of sufficient quality, a new image should be taken before the patient leaves the examination room. Image quality is dependent upon the skill of the system operator, ensuring that pre-defined standard operating procedures are followed. In particular, factors relating to patient positioning with respect to the detector require the patient's cooperation. U.S. 2004/0161141 discusses a method for deducing the orientation of a radiographic image from the digital representation of the image. Such systems can, however, be further improved.

SUMMARY OF THE INVENTION

There may, thus, be a need to provide a technique for enhanced X-ray image inhalation quality monitoring. The object of the present invention is solved by the subject-matter of the independent claims, wherein further embodiments are incorporated in the dependent claims. It should be noted that the following described aspects of method according to the invention apply also for the apparatus, the X-ray imaging system, the computer program element and the computer readable medium according to the invention.

According to a first aspect of the invention, there is provided a method for X-ray image inhalation quality monitoring, comprising the steps of:
a) receiving an X-ray image of a region of interest of a patient;
b) generating a diaphragm line representing a path of a diaphragm in the X-ray image, and generating a rib line representing path of rib bones in the X-ray image;
c) detecting the diaphragm line, and detecting the rib line;
d) assessing the X-ray image for the presence of an intersection condition between (i) the diaphragm line and (ii) the rib line, wherein the intersection condition of the diaphragm line and the rib line is defined according to a intersection condition rule; and
e) comparing the presence of the intersection condition between the rib line and the diaphragm line with a pre-determined X-ray image inhalation quality monitoring rule specifying an image inhalation state in terms of the intersection condition rule, to yield an X-ray image inhalation quality measure.

Therefore, the method has the effect of improving the success rate of medical imaging, and simplifying the assessment process. An algorithm analyses a chest X-ray image, and uses the presence (or not) of an intersection of a rib bone with the diaphragm as an indication that a good quality image has been taken, or not. In addition, there is a benefit that the rejection of lower quality images becomes less dependent upon variations or biases in the skill level of different system operators. Furthermore, the automated quantification of the respiration status of the patient can be integrated into an automated radiological interpretation and reporting process. For example, areas of consolidation in the image, caused, for example, by a condition such as tuberculosis, may require a radiograph to be acquired in an alternative inhalation state, which may be detected. Misinterpretation of such an image can be avoided, and instead a report of an infectious tuberculosis process present in the lung may be generated.

In an embodiment of the method according to the invention, a first rib line has a first intersection condition rule, and a second rib line has a second intersection condition rule different to the first rule. The first and second rules are used for determining the intersection condition. Therefore, an intersection condition may be defined which takes into account different anatomical properties of different ribs, enabling very accurate inhalation quality monitoring rules to be defined.

In another embodiment of the method according to the invention, step b) further comprises step b1):
b1) dividing the X-ray image into a right lung field portion and a left lung field portion; and
wherein in step c), the step of detecting the diaphragm line and the rib line is performed either in the left lung field portion, the right lung field portion, or both; and
wherein steps d) and e) are repeated to enable a left lung X-ray image inhalation quality measure and/or a right lung X-ray image inhalation quality measure to be calculated.

Therefore, useful inhalation quality data can be gathered for a right or a left lung in isolation.

In another embodiment of the method according to the invention, the steps b2), e1), and e2) are provided, comprising:
b2) identifying a consolidated area in a left lung field or a right lung field of the X-ray image; and
e1) if a consolidated area is identified in the left lung field, providing as the X-ray image inhalation quality measure the right lung X-ray image inhalation quality measure; or
e2) if a consolidated area is identified in the right lung field, providing as the X-ray image inhalation quality measure the left lung X-ray image inhalation quality measure.

Therefore, a lung which is unsuitable for use in a lung image quality assessment may be excluded.

According to a second aspect of the invention, there is provided an apparatus for X-ray image inhalation quality monitoring. The apparatus comprises a processing unit. The processing unit is configured to receive an X-ray image of a region of interest of a patient, to generate a diaphragm line representing a path of a diaphragm in the X-ray image, to generate a rib line representing a path of rib bones in the X-ray image, to detect the diaphragm line, and to detect the rib line, to assess the X-ray image for the presence of an intersection condition between (i) the diaphragm line and (ii) the rib line. The intersection condition of the diaphragm line and the rib line is defined according to an intersection condition rule, and wherein the processor is configured to compare the presence of the intersection condition between the rib line and the diaphragm line with a pre-determined X-ray image inhalation quality monitoring rule specifying an image inhalation state in terms of the intersection condition rule, and to yield an X-ray image inhalation quality measure. Therefore, an apparatus is provided having advantages similar to the first aspect discussed above.

In an embodiment of the apparatus according to the invention, a first rib line has a first intersection condition rule, and a second rib line has a second intersection condition rule different to the first rule, and wherein the first and second rules are used for determining the intersection condition. Therefore, an intersection condition may be defined which takes into account different anatomical properties of different ribs.

In another embodiment of the apparatus according to the invention, the processing unit is further configured to divide the X-ray image into a right lung field portion and a left lung field portion, to detect the diaphragm line and the rib line in the left lung field portion, the right lung field portion, or both, and to repeat the detection to enable a left lung X-ray image inhalation quality measure and/or a right lung X-ray image inhalation quality measure to be calculated. Therefore, useful inhalation quality data can be gathered for a right or a left lung in isolation.

In another embodiment of the apparatus according to the invention, the processing unit is further configured to identify a consolidated area in the left lung field or the right lung field of the X-ray image, and wherein the processing unit is configured to provide, as the X-ray image inhalation quality measure, the right lung X-ray image inhalation quality measure, if a consolidated area is identified in the left lung field; or to provide the X-ray image inhalation quality measure as the left lung X-ray image inhalation quality measure, if a consolidated area is identified in the right lung field. Therefore, a lung which is unsuitable for use in a lung image quality assessment may be excluded.

In another embodiment of the apparatus according to the invention, the processing unit is further configured to detect a clavicular line representing the path of a clavicle in the X-ray image, to generate a clavicular dividing line representing a line in the X-ray image which divides the clavicular line, and to assess the X-ray image for the presence of a clavicular intersection condition of the clavicular dividing line with the diaphragm line, wherein the intersection condition rule is defined as the intersection point of the clavicular dividing line with the diaphragm line. Therefore, an intersection condition rule may be provided which is related to more bones in the patient's anatomy, enabling an improvement in measurement accuracy.

In another embodiment of the apparatus according to the invention, the pre-determined X-ray image inhalation quality monitoring rule is that a positive X-ray image inhalation quality measure is output when the posterior portion of a tenth rib line satisfies an intersection condition rule defining that the tenth rib intersects with the diaphragm line. Therefore, a standard inhalation quality assessment parameter is provided.

Another embodiment of the apparatus according to the invention further comprises an output unit. The output unit is configured to display the X-ray image inhalation quality measure. Therefore, an inhalation quality measure can be displayed to a medical professional.

In another embodiment of the apparatus according to the invention, the processing unit is further configured to receive imaging guideline configuration information, comprising rib counting configuration information, and to compare a number of further rib lines located in a lung field to the rib counting configuration information, to yield a guideline inhalation status comparison. The output unit is further configured to display the guideline inhalation status comparison. Therefore, in this way, the apparatus use standard information from a regulatory body, and automatically apply this information to X-ray images as they are taken.

According to a third aspect of the invention, there is provided an X-ray imaging system.

The X-ray imaging system comprises an X-ray image acquisition device, with an X-ray source and an X-ray detector, and an apparatus as previously described.

The X-ray image acquisition device is configured to acquire X-ray image data of a region of interest of a patient, and to provide the X-ray imaging data to the apparatus.

Therefore, an X-ray imaging system having the ability to provide a lung image quality assessment to a user is provided.

According to a fourth aspect of the invention, there is provided a computer program element for controlling an apparatus as previously described. When being executed by the processing unit, the computer program element is adapted to perform the method steps as previously described.

According to a fifth aspect of the invention, there is provided a computer-readable medium having stored the computer program element as previously described.

In this text, the term "region of interest of a patient" means a section of a patient which is imaged by an X-ray imaging apparatus. In the case of a chest examination, the region of interest is located below the neck and above the diaphragm of the patient, although it will be appreciated that the region of interest may be imaged from many different angles. For example, a posterior-anterior, or an anterior-posterior imaging approach are commonly used. The region of interest can also be a lateral section through the patient from either side. The region of interest can be a portion of the chest image as an angle by a mobile X-ray imaging apparatus, for example.

In this text, the term "diaphragm" can refer to an X-ray projection of a diaphragm onto an X-ray detector, hence forming an X-ray image of the diaphragm (for example from the posterior or anterior body direction). Thus, the term "diaphragm line" defines a path in the X-ray image which tracks the shape of the trace of a diaphragm in the X-ray image. The diaphragm typically appears as a cup-shaped boundary at the bottom of the lung lobes, although the boundary can move, dependent upon the extent to which the chest cavity is enlarged.

In this text, the term "rib" or "clavicle" can refer to an X-ray projection of a rib onto an X-ray detector, hence forming an X-ray image of the rib (for example, also from the posterior, or anterior body direction). Thus, the term "rib lines" defines lines of the X-ray image which correspond to the shape of a rib bone in a patient.

Dependent upon the imaging angle, and the image type, and of the extent of patient inspiration or expiration, the rib line may be more or less curved, and may intersect with the diaphragm, or other rib lines.

In this text, the term "intersection condition" defines a situation in which the region of the X-ray image containing a section of the diaphragm coincides with a section of the X-ray image that contains a section of image containing a rib line. Thus, the "intersection" is not a physically occurring intersection in a patient's body, but rather an intersection condition resulting from a geometric projection of an X-ray beam through a patient thorax, thereby projecting a trace of the diaphragm and at least one rib onto an X-ray detector to form a rib line or a diaphragm line.

In this text, the term "intersection condition rule" defines a logical condition defining whether or not a rib line overlays a diaphragm line, or vice versa. For example, it may be considered that an intersection condition can securely be defined for the eighth rib, where the lateral 4/7th space of the eighth rib lies within the outer half of a diaphragm. If this condition is met, then the intersection condition is declared to be true. If this condition is not met, then the intersection condition is defined to be false. It will be appreciated that many intersection condition rules could be envisaged, involving the particular intersection extent between the diaphragm and the rib. Different intersection condition rules are possible for anterior-posterior (AP), posterior-anterior (PA), or lateral views, or different X-ray source or detector imaging angles. Alternatively, or in addition, the intersection condition rules may be varied dependent upon patient-specific data, such as the age, sex, or body morphology of the patient.

In this text, the term "pre-determined X-ray image inhalation quality monitoring rule" enables the determination of whether or not a good, or a bad, image is present. The X-ray image inhalation quality monitoring rule can use one, or a number, of rib intersection conditions to determine whether a good quality X-ray image is present. In its simplest form, the predetermined X-ray image inhalation quality monitoring rule only requires a true intersection condition between one rib, for example, the tenth rib and the diaphragm. In more complex, predetermined X-ray image inhalation quality monitoring rules, the condition for a good X-ray image inhalation quality to be present can be based on the intersection of several ribs with a diaphragm, for example. The rule can be a basic logical condition, or a more complex assessment involving continuous quantities such as probabilities.

Therefore, it is seen that a basic idea of the invention is to identify automatically the presence of a crossing point between the diaphragm and a rib line in an X-ray image. The presence of this crossing point may be used in a further test to define whether or not such a crossing point satisfies an intersection condition rule, and a pre-determined X-ray image inhalation quality monitoring rule, to enable the deduction of an X-ray image inhalation quality measure. This enables the automation of the assessment of a subject's inhalation state, for the purpose of preventing potential mistakes in the evaluation of X-ray image quality.

BRIEF DESCRIPTION OF THE DRAWINGS

Exemplary embodiments of the invention will be described in the following with reference to the following drawings:

FIG. 5 shows an apparatus according to a second aspect.

DETAILED DESCRIPTION OF EMBODIMENTS

Chest radiography is a commonly performed clinical imaging examination. Chest radiography plays an important role in the detection and diagnosis of diseases of the thorax. The quality of images acquired by chest radiography can be defined, for example, according to: the inclusion of appropriate anatomy within the field of view, the contrast of structures of interest with respect to the background signal, and aspects of the positioning of the patient's thorax with respect to the X-ray equipment. The evaluation of image quality is focused on meeting minimum requirements defined for each type of examination. The assessment of these minimum requirements depends upon the skill of a system operator. Typically, pre-defined standard operating procedures should be followed. In particular, a patient's positioning with respect to the X-ray detector requires the patient's cooperation.

A typical projection geometry used in chest radiography is the posterior-anterior view (PA). In this view, the X-ray source is positioned such that the X-ray beams enter through the posterior aspect of the chest, and exit the anterior of the patient, before reaching the detector. Diagnostic guidelines, such as those defined by the European Commission in "European Guidelines on Quality Criteria for Diagnostic Radiographic Images, 1996" define that the acquisition should take place at maximum patient inspiration, with the suspension of respiration. The reason for this is that the projected area of the lung parenchymal tissue on the image detector is maximized thereby, avoiding the superposition of other opaque structures such as abdominal tissues. The aeration of the visualized parenchymal tissues is maximized, and vascular crowding regions are shifted out of the imaged lung field. The basic mechanism of breathing is that when the diaphragm contracts (pulling the bottom of the chest cavity down), the chest cavity enlarges, reducing the pressure inside the chest cavity. To equalize the pressure, air rushes into the lungs. When the diaphragm relaxes (moving up), the elasticity of the lungs, and the chest wall, cause the chest wall to contract, thus pushing air out of the lungs.

Figure 1A:
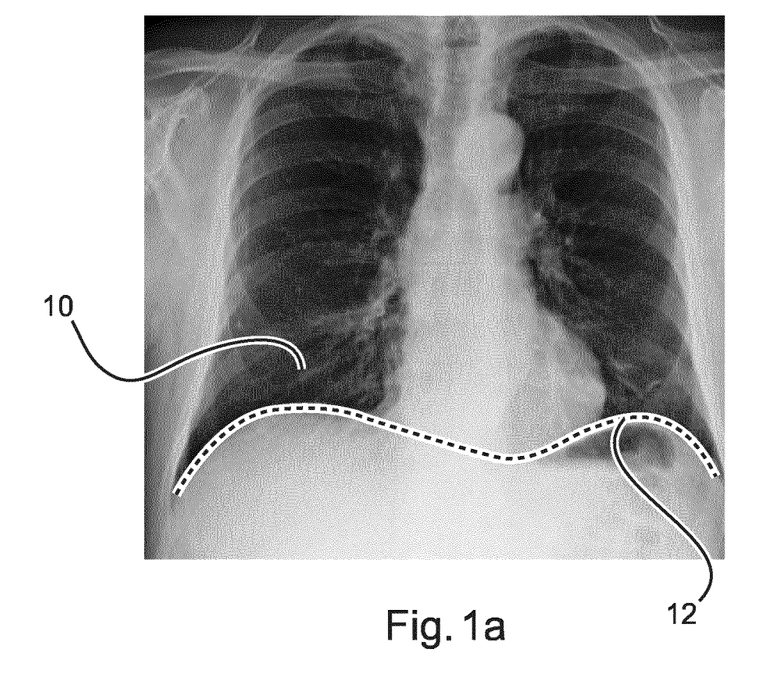
FIGS. 1a) and 1b) show an X-ray image of a thoracic cavity in inspiration and expiration, respectively.
Figure 1B:
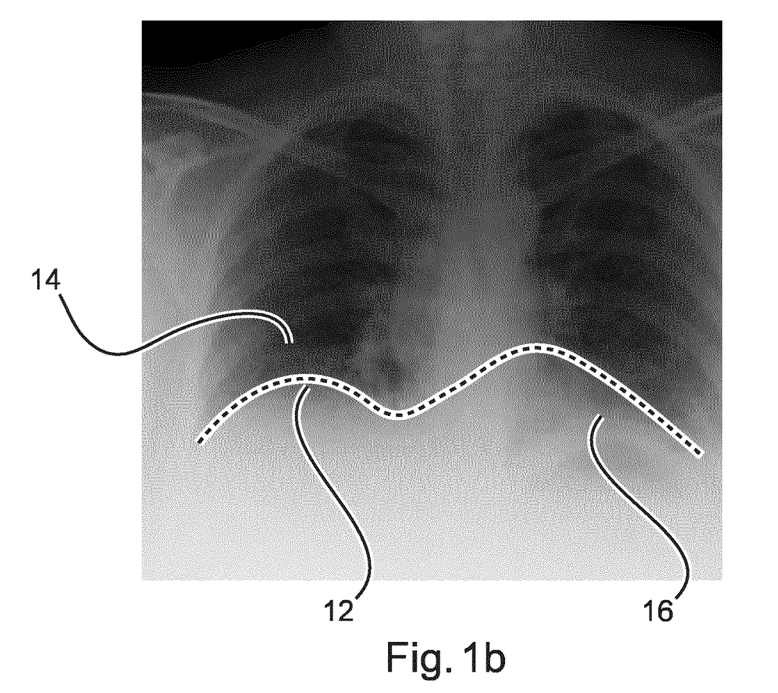

FIG. 1 shows X-ray images showing differences in image quality between images of the same patient which were acquired during inhalation and exhalation states.

FIG. 1a) shows a lung in inspiration. In the inspiration state, the curve of the rib bones from anterior to posterior can clearly be seen, and the lung field 10 is enlarged, because the diaphragm 12 pulls the entire structure of the thorax down. This imaging state is the preferred state for a good-quality thorax X-ray.

FIG. 1b) shows a lung in exhalation. The lung field 14 is smaller. In addition, it is not clear in FIG. 1b) whether or not the opacified area 16 relates to an underlying medical condition, or is simply related to the vascular bundle of vessels around the heart.

Therefore, a medical professional would prefer to image a lung in the state shown in FIG. 1a).

Figure 2A:
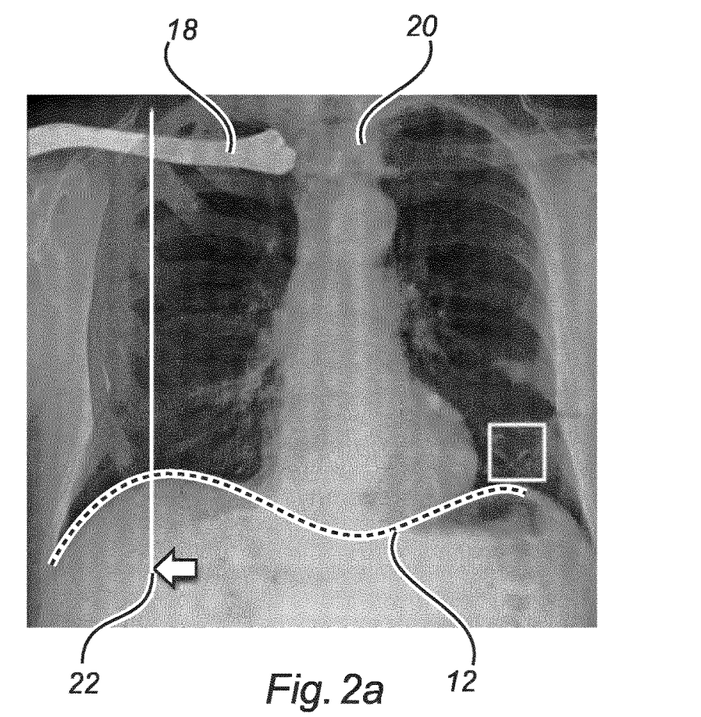
FIGS. 2a) and 2b) show a clavicular line and diaphragm intersection technique.

FIG. 2a) shows a representation of the lung of FIG. 1a) in inspiration. The right clavicle 18 is at a right angle to the spinal column 20. These bones have been highlighted. A clavicular dividing line 22 has been superimposed, and it is seen that the line intersects the diaphragm 12. The point at which the clavicular dividing line 22 intersects the diaphragm is a previously-known lung image quality monitoring measure.

Figure 2B:
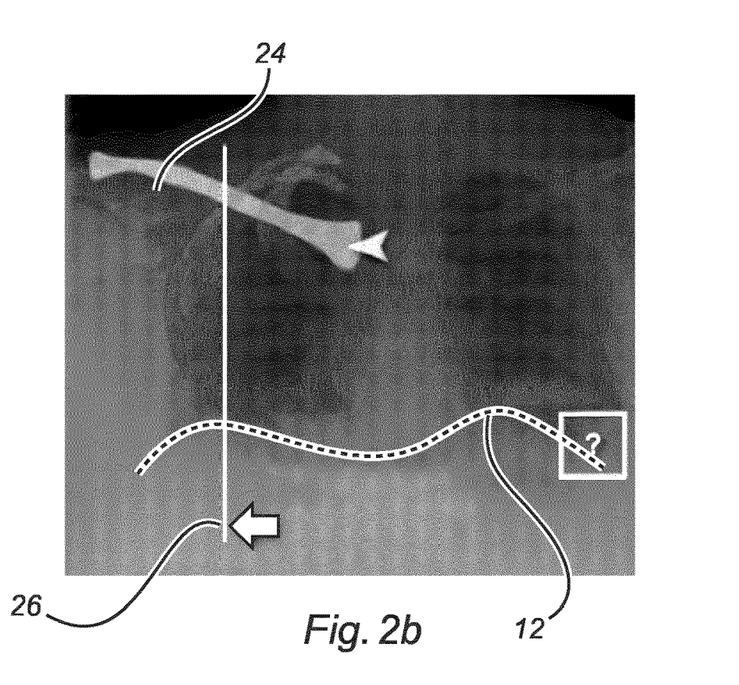

FIG. 2b) shows a representation of the lung of FIG. 1b) in expiration. The right clavicle 24 is now shown at an angle to the spinal column 20, and hence the clavicular dividing line 26 intersects the diaphragm 12 at a more medial point, compared to the situation in FIG. 2a).

Figure 3:
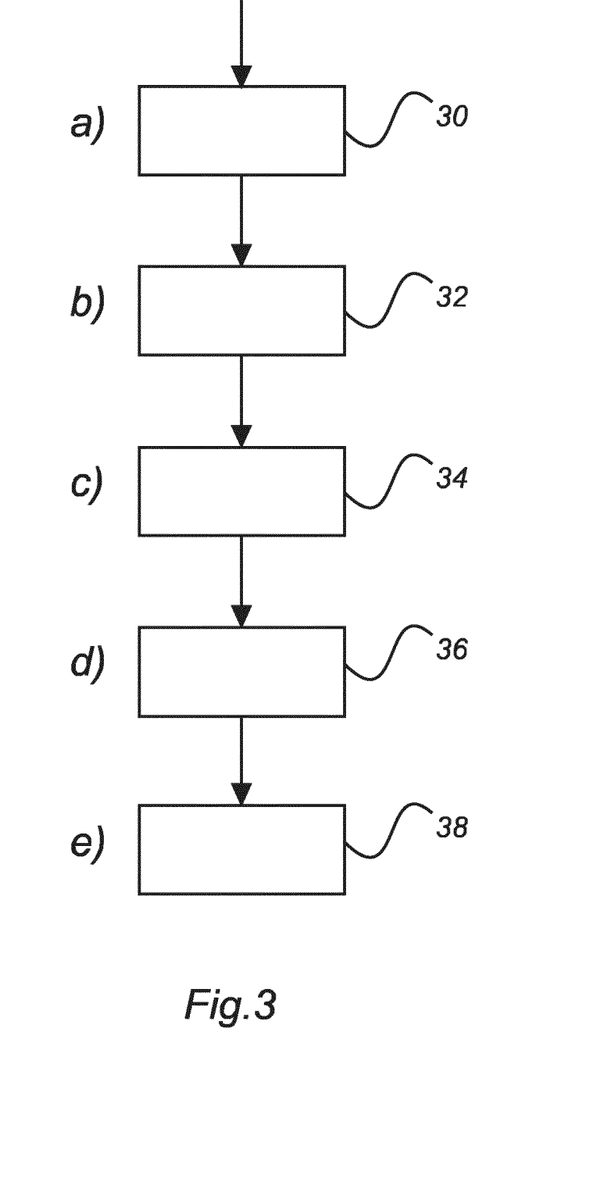
FIG. 3 shows a method according to a first aspect.

Presently, diagnostic guidelines referring to lung shadow and diaphragm interactions depend on the skill level of the operator in controlling the many factors of acquisition which can impact image quality. For example, the timing of the X-ray exposure should coincide with the maximum inspiration phase of the patient's breathing cycle. If the radiographer does not adequately instruct the patient, or if the patient has certain difficulties in carrying out the instructions appropriately, then the quality of the X-ray image can be negatively affected. Presently, after acquisition, the image is visually evaluated by the operator performing the image acquisition, to determine whether or not the quality of the X-ray image is sufficient to be sent for further diagnostic interpretation. Therefore, the operator's skill level is also an important factor in deciding upon image quality, and the decision about whether or not to reject or accept a specific image before the patient is left the imaging room. Thus, an improved method of X-ray image assessment is required. Therefore, according to a first aspect of the invention, there is provided a method for X-ray image inhalation quality monitoring. The method comprises the steps of:

a) receiving 30 an X-ray image of a region of interest of a patient;
b) generating 32 a diaphragm line representing a path of a diaphragm in the X-ray image, and generating a rib line representing a path of rib bones in the X-ray image;
c) detecting 34 the diaphragm line, and detecting the rib line;
d) assessing 36 the X-ray image for the presence of an intersection condition between (i) the diaphragm line and (ii) the rib line, wherein the intersection condition of the diaphragm line and the rib line is defined according to a intersection condition rule; and
e) comparing 38 the presence of the intersection condition between the rib line and the diaphragm line with a pre-determined X-ray image inhalation quality monitoring rule specifying an image inhalation state in terms of the intersection condition, to yield an X-ray image inhalation quality measure.

FIG. 3 illustrates the method according to the first aspect. In step a), the X-ray image is typically received from a digital flat-panel X-ray detector. This assumes that a process of positioning the patient in a desired position in an X-ray detector has taken place, and that an X-ray image has been taken.

Alternatively, the X-ray image may be received from a digital scanning apparatus. A legacy X-ray machine may be used to provide a film-exposure of the region of interest, which may then be digitized and analyzed for exposure quality according to this aspect of the invention.

In step b), a diaphragm line is identified in the X-ray image. Typically, when the region of interest is a human thorax, the diaphragm follows a curved path through the bottom of the thorax area. The diaphragm divides different textures of tissue, and has a distinct shape, having a right-hand-side "dome" which is slightly higher than a dome of the left side of the diaphragm. Therefore, a line following the path of the diaphragm in the X-ray image is amenable to detection by image processing techniques. Although a human diaphragm is a single, connected boundary, as illustrated in FIG. 1, it is possible for practical purposes to detect distinct sections of the diaphragm, such as a left section and a right section.

Optionally, the diaphragm may be detected by gradient detection, texture detection of regions inside the thorax, a water filling algorithm, or by deploying knowledge learned from training images concerning the expected shapes to be found in the image. The shape of the diaphragm follows a curved line, and is thus amenable to modelling using a spline approach.

The rib line can also be extracted using alternative image processing techniques. Optionally, the rib lines may be numbered using a labelling algorithm.

In step c), there is a step of detecting the diaphragm line, and detecting the rib line. It is known to a person skilled in the art that the identification of the outline of rib shadows and the location of the diaphragm border delineating the bottom of the lung shadow can be extracted from an X-ray image.

Optionally, a geometrical reasoning engine may infer the number of lower rib sections (both posterior and anterior) whose shadows are projected above the diaphragm line, and label the rib lines according to their rib position. Conventionally, the rib nearest a patient head is denoted "1". The "true ribs" depend downwards as ribs 1 to 7. The "false ribs" 8-12 depend onwards. Ribs 11-12 are sometimes known as the "floating ribs".

In step d), a rib intersection condition is identified. A rib intersection condition means, in its simplest form, that in the X-ray image, one rib line shares a point of the X-ray image with one diaphragm line.

Optionally, the presence of a rib intersection condition is defined according to the number of the rib. Different-numbered ribs may be defined to cross the diaphragm, or not, dependent upon various rules, to be discussed further below. It is not excluded that a rib intersection condition may involve the intersection of more than one rib with the diaphragm.

Step e) is applied following confirmation of the presence of an intersection condition of the diaphragm line and the rib line. In a simple example, it could be the case that the presence of any intersection of a specific rib line with the diaphragm indicates that the lung field is sufficiently expanded. This will be the case for the higher-numbered ribs, for example. Some rib lines will, however, be located such that even if they intersect with the diaphragm, the lung field still will not be enlarged sufficiently to enable a conclusion that a good quality image has been taken. Therefore, it can be seen that the pre-determined X-ray image inhalation quality rule applies a further filter on whether or not a good-quality X-ray image has been taken.

According to an embodiment, which may be combined with any other embodiment in this description, in step b), a plurality of rib lines is generated in the X-ray image, wherein each of the plurality of rib lines represents the line of a different rib. In the case that a plurality of rib lines is generated, in step c), the plurality of rib lines is detected. In step d), a rib line from the plurality of rib lines is assessed for intersection with the diaphragm line. In this case, the intersection condition rule may comprise details of the intersection conditions of one, or a plurality of rib lines.

Once it has been confirmed that an intersection of a rib line and a diaphragm line is present, and that such an intersection satisfies the condition for a good-quality lung field to be shown in the X-ray image, the X-ray image inhalation quality measure is output.

Optionally, there is a step f) of outputting the X-ray image inhalation quality measure.

Optionally, in step f), the X-ray image inhalation quality measure is output on a computer display screen.

Optionally, the X-ray image inhalation quality measure is a simple binary indicator indicating either that the image is of good or bad quality, implying that a retake of the X-ray image is not, or is needed. This allows simpler presentation of the result of the determination.

Optionally, in step f), the X-ray image inhalation quality measure is output as an illuminated warning light, or a warning sound.

Optionally, in step f), the X-ray image inhalation quality measure is output as a bitmap "watermark" inserted in a portion of an X-ray image provided by an X-ray apparatus.

Optionally, the X-ray image inhalation quality measure is a discretized category, for example selected from the group of "bad, medium, good".

Optionally, the intersection condition rule may be customized to an imaging angle of an X-ray source and/or detector. There is the step of inputting an imaging apparatus setup angle. There is a step of choosing the intersection condition rule on the basis of the input imaging apparatus setup angle. In this way, changes in the image caused by geometric projection effects may be accounted for.

Optionally, the X-ray image inhalation quality measure is a continuous value, for example a percentage. This allows an experienced operator to gauge the quality of the image themselves.

According to an embodiment, the intersection condition rule and/or the pre-determined X-ray image inhalation quality monitoring rules may be provided as data records linked to specific imaging standards, such as the "European Guidelines on Quality Criteria for Diagnostic Images", to enable regional or national imaging standards to be followed. Such standard rules are supplied in a data carrier format such as a CD-ROM, or supplied via a download or an update from the internet.

According to an embodiment, the intersection condition rule and/or the pre-determined X-ray image inhalation quality monitoring rules may be pre-programmed by a medical imaging professional, either to a pre-defined standard, or to a specific protocol required by a healthcare facility. The parameters of the rules, as discussed below, may be pre-programmed using a computer interface.

Figure 4A:
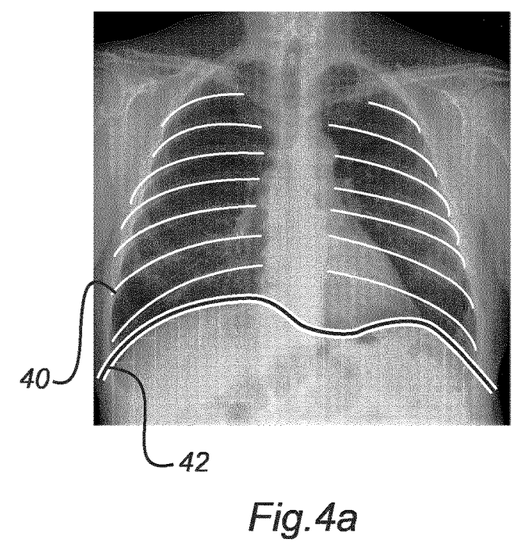
FIGS. 4a) and 4b) show a thorax after having been processed with an exemplary version of the algorithm discussed herein.
Figure 4B:
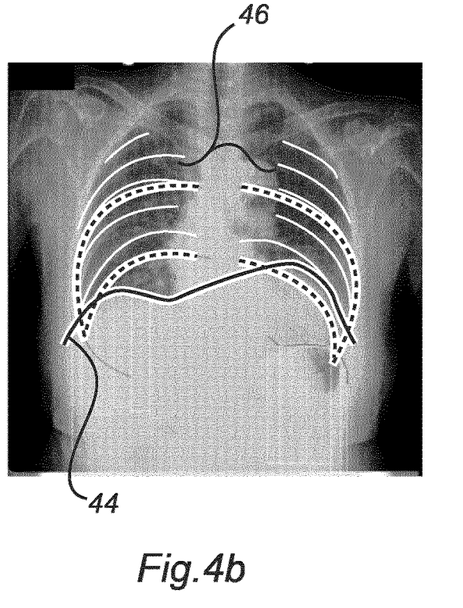

FIGS. 4a) and 4b) shows PA chest radiographs in an inspired, and expired condition, respectively. Rib lines and diaphragm lines generated and detected according to an annotation process known in the art, and discussed above show an exemplary application of the above method, to be discussed in detail below. The annotated line 30 is the diaphragm line. Annotated line 32 represents the sixth rib. Annotated line 34 represents the eighth rib. Annotated line 36 represents the tenth rib. Ribs considered to intersect with the diaphragm line 30 are represented with a dotted line; otherwise, the line is solid.

In the illustrated case, an intersection condition rule has been applied wherein if the anterior aspect of the sixth rib intersects with the diaphragm, then it is considered to intersect with the diaphragm line, and is dotted.

An alternative intersection condition rule, which is not illustrated, is that is more than a pre-defined portion of the posterior aspect of the eighth, ninth, or tenth ribs are located below the diaphragm, they are considered to intersect.

FIG. 4a) shows a thoracic X-ray showing good-quality inspiration. In this case, the intersection condition rule for the sixth rib is that the anterior aspect of the sixth rib intersects with the diaphragm line. In FIG. 4a), the method does not find the intersection condition satisfied, because the sixth rib 40 does not intersect the diaphragm line 42. Therefore, no dotted lines are shown. Furthermore, in this situation, the pre-determined X-ray image inhalation quality monitoring rule defines that a "good quality" image is present, when the intersection condition rule for the sixth rib is not met, enabling the provision of an X-ray image inhalation quality measure to a user.

FIG. 4b) shows a thoracic X-ray showing poor-quality inspiration. In the case of FIG. 4b), the anterior aspect of the sixth rib does intersect with the diaphragm line 44. Therefore, the intersection condition is met, and so the sixth rib line 46 is labelled as a dotted line. As in FIG. 4a), the pre-determined X-ray image inhalation quality monitoring rule defines that a "good quality" image is present, when the intersection condition rule for the sixth rib is not met. Therefore, it is indicated that a "bad quality" image is present, because the sixth rib does intersect with the diaphragm line, accordingly enabling the provision of an X-ray image inhalation quality measure to a user.

FIG. 4b) also shows that the extreme portion (tip) of a third rib intersects with the diaphragm line. An additional third rib intersection condition rule could be defined, for example, that would state that the third rib was only found to intersect the diaphragm line when the intersection of the third rib and the diaphragm was within the medial 50% of the third rib. Thus, "false negative" results owing to the incidental intersection of the tip of a third rib could be prevented.

In simple words, the intersection condition rule can be considered to answer the question, for an interrogated rib, "does this rib intersect with the diaphragm?". The pre-determined X-ray image inhalation quality monitoring rule may be considered to proceed to ask the question "does the fact of this rib satisfying the intersection condition rule mean that a poor quality image is present?". This determination accordingly enables the provision of an X-ray image inhalation quality measure to a user.

Therefore, in FIG. 4, automatically detected rib centrelines and diaphragm locations have been used to quantify the inspiration state of the subjects, and to establish resulting metrics of image quality. The labelling of individual rib lines are defined based on rules defined, per rib, dependent upon the presence of an intersection of the rib, and the diaphragm.

In FIG. 4, the eighth, ninth, and tenth posterior ribs are tested for intersection with the diaphragm. In this example, a rib is considered to be inside the lung field either if it does not intersect, or if its intersection is in the lateral 4/7 of the diaphragm line. This is an example of an intersection condition rule.

Proceeding, the lowest rib with all its upper ribs being insider the lung field is determined (the lung field may be easily segmented, as is known to the person skilled in the art). According to imaging guidelines, the lowest rib with all its upper ribs being insider the lung field should be the tenth rib, on both sides, for good inspiration quality. This is an example of a pre-determined X-ray image inhalation quality monitoring rule.

According to an embodiment, the pre-determined X-ray image inhalation quality monitoring rule is that a positive X-ray image inhalation quality measure is output when the posterior portion of a tenth rib line satisfies an intersection condition rule defining that the tenth rib intersects with the diaphragm line.

Figure 5A:
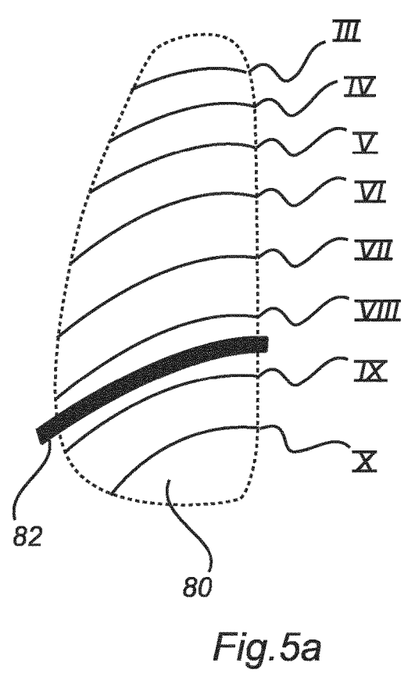
FIGS. 5a) and 5b) show a simplified line representation of the thorax of FIG. 4.

FIGS. 5a) and 5b) show a simplified version of FIGS. 4a) and 4b), with the surrounding image stripped away. For ease of understanding, the anterior portions of the ribs are not shown in this representation. The anterior portions would appear as overlaid portions or the ribs. The numbering of the roman numerals refers to the standard rib level notation familiar to a medical professional.

FIG. 5a) shows a schematic of the right half of a thorax cavity with a level of inspiration necessary to provide a "good quality" image. The schematic shows lung field 80. Seven rib lines, numbered according to medical convention, are displayed in the lung field. A diaphragm line 82 divides the eighth rib line from the ninth rib line. The diaphragm 82 does not cross the rib line, and hence an intersection condition rule is false.

Figure 5B:
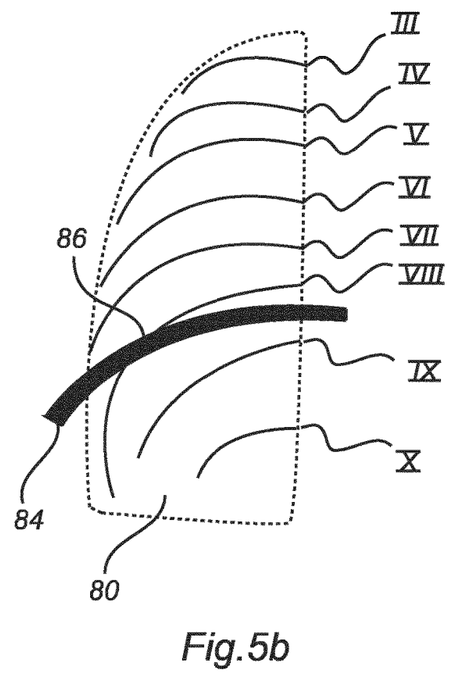

FIG. 5b) shows a schematic of the right half of a thorax cavity with a level of inspiration which would result in a "poor quality" image. Eight rib lines, numbered according to medical convention, are displayed in the lung field. A diaphragm line 84 divides the eighth rib line from the ninth rib line. The diaphragm 84 crosses the eighth rib line at point 86. If, in this case, the intersection condition rule is simply that any crossing of the eighth rib line and the diaphragm line causes the intersection condition rule to be satisfied, then in this case the intersection condition rule is satisfied, and the eighth rib is defined as crossing the diaphragm line. Furthermore, it may be assumed in this example that an image inhalation state is defined as being of poor quality if the eighth rib line crosses the diaphragm line. Thus, in this case, the detection algorithm would declare that a poor quality image was present. A more complex image inhalation state could be defined with rules combining the crossing state of multiple ribs, or to the lateral extent along a rib or a diaphragm at which the rib or diaphragm is crossed.

According to an embodiment of the method, there is a step of labelling (numbering) the rib elements, for example, in numerical order.

According to an embodiment of the method, the intersection condition rule comprises a first intersection condition rule to be applied to an initial labelled rib, and a second intersection condition rule to be applied to a subsequent labelled rib. The first and second rib intersection condition rules are different.

Alternatively, the first and second rib intersection condition rules are the same. This is useful in the case where the first and second ribs are on the same level of the rib cage, but on right and left sides of the rib cage.

According to this embodiment, two labelled ribs have different intersection rules applied to them, in order to determine the presence of two or one intersections with the diaphragm. The fact that different intersection rules may be applied to different ribs means that the natural anatomical variation of higher-numbered ribs, as compared with lower-numbered ribs, may meaningfully be taken account of to provide a more accurate quality estimate.

According to an embodiment of the method, the intersection condition rule additionally comprises a third, fourth, fifth, sixth, seventh, eighth, ninth, tenth, eleventh, or twelfth intersection condition rule. These intersection condition rules correspond, respectively, to the numbering of ribs in a human rib cage. It is not necessary that all of the intersection condition rules in the foregoing list of twelve intersection condition rules are present, and any combination of them may be made to beneficial effect, dependent on the consideration of what combination of anatomical features represents a good quality X-ray image.

According to an embodiment of the method, an intersection condition rule as defined above comprises a pixel of a rib line having at least one identical pixel location to a pixel of the diaphragm line in the X-ray image.

According to an embodiment of the method, the intersection condition rule is considered not satisfied if the intersection is located in the lateral 2/7, 3/7, 4/7, 5/7, 6/7 of the diaphragm line.

Image processing algorithms can be applied to distinguish portions of the rib bone in an X-ray image. For example, the anterior and posterior portions may be distinguished by examining changes in curvature of the rib bone.

According to an embodiment of the method, the intersection condition rule comprises an anterior intersection condition rule. This means that a decision about the intersection of a rib with the diaphragm is made using image information relating to the anterior portion of the rib only. The anterior condition rule may optionally be different, for each rib. The anterior intersection condition rule may optionally be different, for the right side or the left side of the rib-cage.

According to an embodiment of the method, the intersection condition rule comprises a posterior intersection condition rule. This means that a decision about the intersection of a rib with the diaphragm is made using image information relating to the posterior portion of the rib only. The posterior condition rule may optionally be different, for each rib. The posterior intersection condition rule may optionally be different, for the right side or the left side of the rib-cage.

According to an embodiment of the method, the intersection condition rule comprises an anterior and/or a posterior intersection condition rule. The anterior and/or the posterior intersection condition rule may optionally be different, for each rib. The anterior and/or the posterior intersection condition rule may optionally be different, for the right side or the left side of the rib-cage.

According to an embodiment of the method, the intersection condition rule comprises, using a horizontal anterior view, an intersection of the seventh rib line with the diaphragm line, such that six ribs appear in the lung field above the diaphragm line.

According to an embodiment of the method, the intersection condition rule comprises, using a horizontal posterior view, an intersection of the tenth rib line with the diaphragm line, such that nine ribs appear in the lung field above the diaphragm line.

According to an embodiment of the method, a width measure of an examined rib is stored, and an intersection condition is deemed to be present when a segment of a rib line moves within a width of 100%, 50%, 25%, 10%, or 1% of the width of the width measure of the examined rib.

According to an embodiment of the method, a pre-defined quality monitoring rule is provided which defines that a poor quality image is present if the intersection condition rule is satisfied.

According to an embodiment of the method, a pre-defined quality monitoring rule is provided which defines that a poor quality image is present if the intersection condition rule is satisfied.

According to an embodiment of the method, a pre-defined quality monitoring rule is provided which combines a plurality of per-rib intersection condition rules in order to determine whether or not a poor quality image is present.

According to an embodiment of the method, the pre-defined quality monitoring rule comprises a numerical likelihood value.

According to an embodiment of the method, the X-ray image is taken using a posterior-anterior (PA), an anterior-posterior (AP), or a lateral view.

According to an embodiment of the method, image view direction information is provided, and specific intersection condition rules and specific X-ray image inhalation quality rules may be provided for each view direction. Therefore, an optimum image result may be assured, regardless of the image view direction.

According to an embodiment of the method, there is provided a method as previously described wherein each rib line has a specific intersection condition rule used for determining the intersection condition. In the case where a plurality of rib lines is provided, each rib line also has a specific intersection condition rule used for determining the intersection condition.

According to an embodiment of the method, the pre-determined X-ray image inhalation quality monitoring rule determines whether or not a twelfth, eleventh, tenth, ninth, eighth, sixth, or fifth ribs intersects with the diaphragm.

According to an embodiment of the method, step b) further comprises step b1):
b1) dividing the X-ray image into a right lung field portion and a left lung field portion;
wherein in step c), the step of detecting the diaphragm line and the rib line is performed either in the left lung field portion, the right lung field portion, or both;
wherein steps d) and e) are repeated to enable a left lung X-ray image inhalation quality measure and/or a right lung X-ray image inhalation quality measure to be calculated.

According to this embodiment, patients with deformities, or for whom imaging is not possible on one side, may still have an assessment of image quality made, using the X-ray image inhalation quality measure defined just for one lung.

According to an embodiment of the method, step e) further comprises the step of finding a ratio of the left lung X-ray image inhalation quality measure and the right lung X-ray image inhalation quality measure.

Thus, according to this embodiment, an asymmetry in the image may be identified from the calculated right/left ratio.

According to an embodiment of the method, the method further comprises the steps b2) and e1), and e2):
b2) identifying a consolidated area in a left lung field or a right lung field of the X-ray image;
e1) if a consolidated area is identified in the left lung field, providing as the X-ray image inhalation quality measure the right lung X-ray image inhalation quality measure; or
e2) if a consolidated area is identified in the right lung field, providing as the X-ray image inhalation quality measure the left lung X-ray image inhalation quality measure.

If a condition such as tuberculosis is present in thorax of a patient, there can be large areas of consolidation (areas of lung tissue that are filled with liquid). Thus, in a radiograph acquired in the exhalation state, opacified regions are observed, and might be misinterpreted. According to this embodiment of the invention, it is possible to exclude from the inhalation quality measure a right lung or a left lung if a consolidated area is identified in their respective lung fields. Therefore, if an abnormality is identified (using, for example, an image processing algorithm such as a texture or a shape recognition algorithm). If a lung abnormality is detected, the unaffected lung side can be used as the basis of an X-ray image inhalation quality measure. Such a one-sided measure is often a reliably accurate measure.

According to an embodiment of the method, step b) further comprises step b1):
b1) detecting a clavicular line representing the path of a clavicle in the X-ray image;
wherein step c) further comprises the steps:
c1) generating a clavicular dividing line representing a line in the X-ray image which divide the clavicular line;
c2) assessing the X-ray image for the presence of a clavicular intersection condition of the clavicular dividing line with the diaphragm line;
wherein in step c), the intersection condition rule is defined using the intersection point of the clavicular dividing line with the diaphragm line.

The line of a clavicle bone can be identified using the same algorithm as for the rib line detection, with a minor modification to allow for the difference in radius of curvature of the clavicle, compared to a rib bone. The clavicular dividing line can be found as the bisection of the clavicle bone line, or as a certain proportion along it. The point where the clavicular dividing line intersects with the diaphragm line thus forms a point on the diaphragm line which can serve as a discriminator for whether or not a rib bone is considered to intersect with the diaphragm line. This discriminator is, linked to the overall patient posture. Thus, a detection rule involving the intersection of a clavicular line, and a rib line is provided, providing an opportunity for higher accuracy of detection of poor images.

According to an embodiment of the method, step a) further comprises the steps a3), d3), and g1):
a3) receiving imaging guideline configuration information comprising rib counting configuration information; and further comprising the steps e4) and g1):
d3) comparing the number of further rib lines located in the lung field to the rib counting configuration information to yield a guideline inhalation status comparison;
e1) displaying the guideline inhalation status comparison.

Commonly used intersection condition rules and pre-determined X-ray image inhalation quality rules useful for X-ray image diagnosis can be derived from common medical guidelines, which may be provided on a data carrier or via a network as guideline configuration information.

Accordingly, a patient examination may be compared to a standard imaging guideline in an efficient way.

According to an embodiment of the method, the pre-determined X-ray image inhalation quality monitoring rule states that a positive X-ray image inhalation quality measure should be output when a tenth rib line of the rib line satisfies a tenth rib intersection condition rule.

The intersection of the tenth rib with the diaphragm line is a preferred metric in diagnostic imaging practice.

According to an embodiment of the method, the method according to any preceding example further comprises after step a) the step of:
a4) segmenting the X-ray image.

According to a second aspect of the invention, there is provided an apparatus for X-ray image inhalation quality monitoring.

Figure 6:
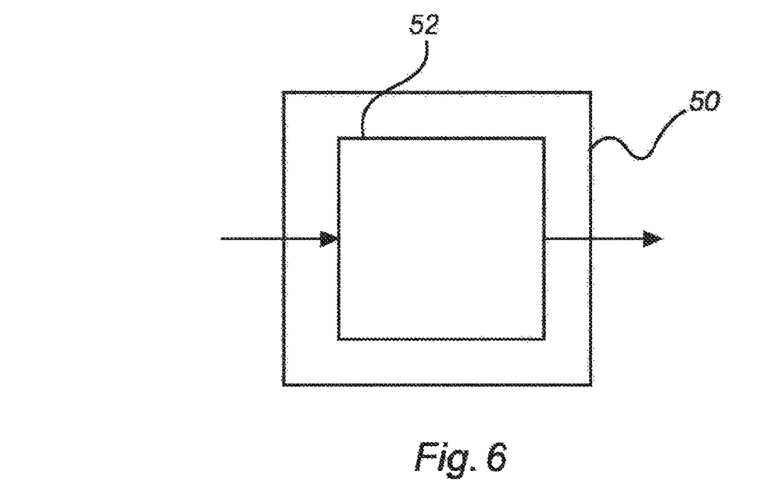
FIG. 6 shows a system according to a third aspect.

FIG. 6 is a block diagram of the apparatus 50 for X-ray image inhalation quality monitoring.

The apparatus 50 comprises a processing unit 52.

An apparatus 50 for X-ray image inhalation quality monitoring, comprising a processing unit.

The processing unit 52 is configured to receive an X-ray image of a region of interest of a patient, to generate a diaphragm line representing a path of a diaphragm in the X-ray image, to generate a rib line representing a path of rib bones in the X-ray image, to detect the diaphragm line, and to detect the rib line, to assess the X-ray image for the presence of an intersection condition between (i) the diaphragm line and (ii) the rib line.

The intersection condition of the diaphragm line and the rib line is defined according to an intersection condition rule, and wherein the processor is configured to compare the presence of the intersection condition between the rib line and the diaphragm line with a pre-determined X-ray image inhalation quality monitoring rule specifying an image inhalation state in terms of the intersection condition rule, and to yield an X-ray image inhalation quality measure.

According to an example, the X-ray image inhalation quality measure is a binary condition. Therefore, if the image is good quality, a true condition is returned, and if the image is bad quality, a false condition is returned.

According to an example, the X-ray image inhalation quality measure is a continuous metric. A continuous metric may enable the inhalation quality measure to be distinguished for different patients, or different conditions.

According to an embodiment, the rib line has a specific intersection condition rule used for determining the intersection condition. In a case where a plurality of rib lines is present, each rib line of the plurality of rib lines has a specific intersection condition rule used for determining the intersection condition.

According to an embodiment, a first rib line has a first intersection condition rule, and a second rib line has a second intersection condition rule different to the first rule, and wherein the first and second rules are used for determining the intersection condition.

According to an embodiment, the intersection condition rule may be customized to an imaging angle of an X-ray source and/or detector. The processor 52 is configured to receive an imaging apparatus setup angle. The processor is configured to select an intersection condition rule on the basis of the input imaging apparatus setup angle. In this way, changes in the image caused by geometric projection effects may be accounted for.

As seen, for example, in FIG. 1, the state of intersection between a rib and a diaphragm line is qualitative, and may vary dependent upon the rib bone considered. Therefore, according to this embodiment, it is possible to ascribe to individual rib lines a specific rib intersection rule which determines whether or not a particular rib line is considered to intersect with the diaphragm. For example, rib number 8 could be considered to intersect if it touches the outer $3/7$ of the diaphragm line, but rib 7 could be considered to intersect if it touches the outer $4/7$ of the diaphragm line.

According to an embodiment, there is provided an apparatus as previously described, wherein the processing unit is further configured to divide the X-ray image into a right lung field portion and a left lung field portion, to detect the diaphragm line and the rib line in the left lung field portion, the right lung field portion, or both, and to repeat the detection to enable a left lung X-ray image inhalation quality measure and/or a right lung X-ray image inhalation quality measure to be calculated. In addition, a right and left inhalation quality comparison may be generated by comparing the left lung field portion and the right lung field portion measurements.

According to this embodiment, it is possible to rely only on measurements of the right lung or the left lung to determine inhalation quality. This is important when the chest X-ray is interrupted by metallic elements, for example hard pacemakers, or other implants or surgical metal work. The assessment of lung inhalation quality may be assessed using only the right or the left lung.

In addition, by comparing the inhalation quality of the right lung and the left lung, an assessment can be made of the symmetry of the inhalation state.

According to an embodiment of the invention, an apparatus is provided as described previously, wherein the processing unit is further configured to identify a consolidated area in a left lung field or a right lung field of the X-ray image, and wherein the processing unit is configured to provide as the X-ray image inhalation quality measure the right lung X-ray image inhalation quality measure if a consolidated area is identified in the left lung field, or to provide the X-ray image inhalation quality measure as the left lung X-ray image inhalation quality measure if a consolidated area is identified in the right lung field. According to an embodiment, there is provided an apparatus as previously described, wherein the processing unit is further configured to detect a clavicular line representing the path of a clavicle in the X-ray image, to generate a clavicular dividing line representing a line in the X-ray image which divides the clavicular line, and to assess the X-ray image for the presence of a clavicular intersection condition of the clavicular dividing line with the diaphragm line. The intersection condition rule is defined as the intersection point of the clavicular dividing line with the diaphragm line.

According to an embodiment, an apparatus is provided as described previously. The pre-determined X-ray image inhalation quality monitoring rule is that a positive X-ray image inhalation quality measure should be output when a tenth rib line of the rib line satisfies a tenth rib intersection condition rule.

It has been found useful to define that a good inspiration condition is present when the tenth rib line crosses the diaphragm.

According to an embodiment, the apparatus 50 as discussed previously is provided, further comprising
an input unit.

The input unit is configured to receive an X-ray image from an X-ray detector. According to an embodiment, the apparatus 50 as discussed previously is provided, further comprising
an output unit.

The output unit is configured to display the X-ray image inhalation quality measure.

Optionally, the X-ray image inhalation quality measure can be displayed as a simple red or green warning light, alarm sound, or a digital or an alphanumeric readout. This enables a simple image quality feedback to be given to a user.

Optionally, the output unit is configured to display the X-ray image inhalation quality measure as a numerical value representing image quality.

According to an embodiment of the invention, the output unit is configured to display the X-ray image inhalation quality measure on an X-ray image itself, either on a digital flat panel display, or introduced onto an analogue X-ray photographic plate. Therefore, a medical professional assessing the image may be given an estimate as to the quality of the X-ray exposure.

According to an embodiment of the invention, an apparatus is provided as discussed previously, wherein the processing unit is further configured to receive imaging guideline configuration information comprising rib counting configuration information, to compare the number of further rib lines located in the lung field to the rib counting configuration information, to yield a guideline inhalation status comparison, and the output unit is further configured to display the guideline inhalation status comparison using the output unit.

In this way, the processing unit may receive information from a regulatory body, and automatically apply this information to X-ray images as they are taken.

Figure 7:
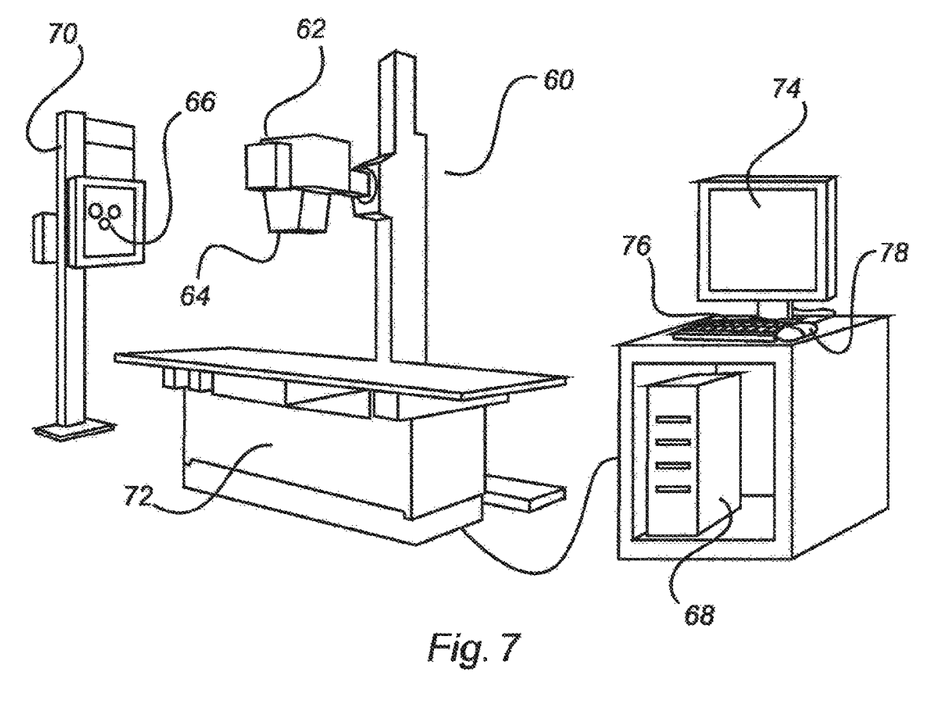
FIG. 7 shows an X-ray imaging system 60.

According to a third aspect of the invention, an X-ray imaging system 60 comprising:
an X-ray image acquisition device 62 with an X-ray source 64 and an X-ray detector 66; and
an apparatus 68 connected to the X-ray detector, and
an output 74.

The X-ray image acquisition device 62 is configured to acquire X-ray image data of a region of interest of a patient, and to provide the X-ray imaging data to the apparatus 68. The apparatus 68 is configured to operate as discussed in any of the embodiments discussed above. The apparatus 68 is configured to output an X-ray image inhalation quality measure to a user via the output 74.

FIG. 7 shows an X-ray imaging system 60. The system comprises an X-ray source 62, typically, of the rotating anode type. The X-ray source 62 may be positioned so that radiation is emitted in the direction of an X-ray detector 66 (for example of a pixelated flat-panel type), where it is received. The X-ray detector 66 is connected to an apparatus 68 as previously described.

In use, a region of interest of a patient is positioned in front of the X-ray source 62. The source is activated, and an exposure of the patient is made. The apparatus 68 assesses the quality of the image according to a rib intersection rule, and a pre-determined X-ray image inhalation quality rule as discussed above. The apparatus 68 yields an X-ray image inhalation quality measure, which is output to a user on the screen 74. Optionally, the output may be a lamp, or a simple audible warning. Optionally, the apparatus may be part of a computer, such as a PC, provided with input means such as a keyboard 76 and a mouse 78.

Optionally, the X-ray detector 62 may be located in a free-standing detector 70, or in a bed 72. Thus, the thorax of a patient may be imaged in the standing, or sitting position.

According to a fourth aspect of the invention, a computer program element for controlling an apparatus according to one of the previous description is provided, wherein the computer program element is executed by a processing unit, to perform the method steps according to any of the previously described method steps.

According to an aspect of the invention, a computer-readable medium is provided, having stored the program element as previously described.

According to a fifth aspect of the invention, there is provided a computer-readable medium having stored the program element described previously.

A computer program element might therefore be stored on a computer unit, which might also be an embodiment of the present invention. This computing unit may be adapted to perform or induce performance of the steps of the method described above. Moreover, it may be adapted to operate the components of the above-described apparatus. The computing unit can be adapted to operate automatically and/or to execute orders of a user. A computer program may be loaded into a working memory of a data processor. The data processor may thus be equipped to carry out the method of the invention.

This exemplary embodiment of the invention covers both the computer program that has the intervention installed from the beginning, and a computer program that by means of an update turns an existing program into a program that uses the invention.

A computer program may be stored and/or distributed on a suitable medium, such as optical storage media, or a solid state medium supplied together with, or as a part of other hardware, but may also be distributed in other forms, such as via the Internet or other wired or wireless telecommunication systems. However, the computer program may also be presented over a network like the World Wide Web, and can also be downloaded into the working memory of a data processor from such a network.

According to a further exemplary embodiment of the present invention, a medium for making a computer program element available for downloading is provided, which computer program element is arranged to perform a method according to one of the previously described embodiments of the invention.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An apparatus for X-ray image inhalation quality monitoring, comprising:
a processor configured to receive an X-ray image of a region of interest of a patient, generate a diaphragm line representing a path of a diaphragm in the X-ray image, generate a rib line representing a path of rib bones in the X-ray image, detect the diaphragm line and the rib line, and assess the X-ray image for the presence of an intersection condition between the diaphragm line and the rib line,
wherein the intersection condition of the diaphragm line and the rib line is defined according to an intersection condition rule, and wherein the processor is further configured to compare the presence of the intersection condition between the rib line and the diaphragm line with a pre-determined X-ray image inhalation quality monitoring rule specifying an image inhalation state in terms of the intersection condition, and yield an X-ray image inhalation quality measure.

2. The apparatus according to claim 1, wherein a first rib line has a first intersection condition rule, and a second rib line has a second intersection condition rule different than the first intersection condition rule, and wherein the first intersection condition rule and the second intersection condition rule are used for determining the intersection condition.

3. The apparatus according to claim 1, wherein the processor is further configured to divide the X-ray image into a right lung field portion and a left lung field portion, detect the diaphragm line and the rib line in the left lung field portion, the right lung field portion, or both, and repeat the detection to enable a left lung X-ray image inhalation quality measure and/or a right lung X-ray image inhalation quality measure to be calculated.

4. The apparatus according to claim 3, wherein the processor is further configured to identify a consolidated area in the left lung field or the right lung field of the X-ray image, and wherein the processor is configured to provide, as the X-ray image inhalation quality measure, the right lung X-ray image inhalation quality measure if a consolidated area is identified in the left lung field; or provide the X-ray image inhalation quality measure as the left lung X-ray image inhalation quality measure if a consolidated area is identified in the right lung field.

5. The apparatus according to claim 2, wherein the processor is further configured to detect a clavicular line representing the path of a clavicle in the X-ray image, generate a clavicular dividing line representing a line in the X-ray image which divides the clavicular line, and assess the X-ray image for the presence of a clavicular intersection condition of the clavicular dividing line with the diaphragm line, wherein the intersection condition rule is defined as the intersection point of the clavicular dividing line with the diaphragm line.

6. The apparatus according to claim 1, wherein the pre-determined X-ray image inhalation quality monitoring rule is such that a positive X-ray image inhalation quality measure is output when the posterior portion of a tenth rib line satisfies an intersection condition rule defining that the tenth rib intersects with the diaphragm line.

7. The apparatus according to claim 1, wherein
the X-ray image inhalation quality measure is output on a display screen, as an illuminated warning light, or as a warning sound.

8. The apparatus according to claim 7, wherein the processor is further configured to receive imaging guideline configuration information comprising rib counting configuration information, compare a number of further rib lines located in a lung field to the rib counting configuration information, and yield a guideline inhalation status comparison.

9. A method for X-ray image inhalation quality monitoring, comprising:
receiving an X-ray image of a region of interest of a patient;
generating a diaphragm line representing a path of a diaphragm in the X-ray image;
generating a rib line representing a path of rib bones in the X-ray image;
detecting the diaphragm line and the rib line;
assessing the X-ray image for the presence of an intersection condition between the diaphragm line and the rib line, wherein the intersection condition of the diaphragm line and the rib line is defined according to a intersection condition rule; and
comparing the presence of the intersection condition between the rib line and the diaphragm line with a pre-determined X-ray image inhalation quality monitoring rule specifying an image inhalation state in terms of the intersection condition; and
yielding an X-ray image inhalation quality measure.

10. The method according to claim 9, wherein a first rib line has a first intersection condition rule, and a second rib line has a second intersection condition rule different than the first intersection condition rule, and wherein the first intersection condition rule and second intersection condition rule are used for determining the intersection condition.

11. The method according to claim 9, further comprising:
dividing the X-ray image into a right lung field portion and a left lung field portion; wherein detecting the diaphragm line and the rib line is performed either in the left lung field portion, the right lung field portion, or both; wherein assessing and comparing are repeated to enable a left lung X-ray image inhalation quality measure and/or a right lung X-ray image inhalation quality measure to be calculated.

12. The method according to claim 11, further comprising:
identifying a consolidated area in a left lung field or a right lung field of the X-ray image;
if a consolidated area is identified in the left lung field, providing as the X-ray image inhalation quality measure the right lung X-ray image inhalation quality measure; or
if a consolidated area is identified in the right lung field, providing as the X-ray image inhalation quality measure the left lung X-ray image inhalation quality measure.

13. An X-ray imaging system, comprising:
an X-ray image acquisition device with an X-ray source and an X-ray detector; and
an apparatus according to claim 1; wherein the X-ray image acquisition device is configured to acquire X-ray image data of the region of interest of the patient, and provide the X-ray imaging data to the apparatus.

14. A non-transitory computer readable medium having one or more executable instructions stored thereon, which when executed by a processor, cause the processor to perform a method for X-ray image inhalation quality monitoring, the method comprising:
receiving an X-ray image of a region of interest of a patient;
generating a diaphragm line representing a path of a diaphragm in the X-ray image;
generating a rib line representing a path of rib bones in the X-ray image;
detecting the diaphragm line and the rib line;
assessing the X-ray image for the presence of an intersection condition between the diaphragm line and the rib line, wherein the intersection condition of the diaphragm line and the rib line is defined according to a intersection condition rule; and
comparing the presence of the intersection condition between the rib line and the diaphragm line with a pre-determined X-ray image inhalation quality monitoring rule specifying an image inhalation state in terms of the intersection condition; and
yielding an X-ray image inhalation quality measure.

* * * * *